(12) United States Patent
Stehmeier et al.

(10) Patent No.: US 9,366,618 B2
(45) Date of Patent: Jun. 14, 2016

(54) STIFFENING COMPONENT AND METHOD AS WELL AS COMBING TOOL

(75) Inventors: Heiner Stehmeier, Bremen (DE); Pierre Zahlen, Stade (DE); Benjamin Teich, Stade (DE); Helene Guinard, Bremen (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 228 days.

(21) Appl. No.: 13/636,506

(22) PCT Filed: Mar. 23, 2011

(86) PCT No.: PCT/EP2011/001429
§ 371 (c)(1),
(2), (4) Date: Nov. 20, 2012

(87) PCT Pub. No.: WO2011/116940
PCT Pub. Date: Sep. 29, 2011

(65) Prior Publication Data
US 2013/0087273 A1    Apr. 11, 2013

Related U.S. Application Data

(60) Provisional application No. 61/316,389, filed on Mar. 23, 2010.

(30) Foreign Application Priority Data

Mar. 23, 2010    (DE) .......................... 10 2010 012 342

(51) Int. Cl.
*G01N 19/04*    (2006.01)
*B29C 70/54*    (2006.01)
(Continued)

(52) U.S. Cl.
CPC .................. *G01N 19/04* (2013.01); *B26F 1/24* (2013.01);*B29C 70/545* (2013.01); *B32B 38/04* (2013.01); *G01M 3/26* (2013.01); *G01M 5/0033* (2013.01); *Y10T 83/9314* (2015.04);

(58) Field of Classification Search
CPC ... G01M 3/26; G01M 3/2884; G01M 5/0033; G01N 19/08; G01N 19/04; B32B 3/30; B32B 38/04; B29C 66/47; B29C 70/545
USPC ..................... 156/64; 73/37, 40, 86
See application file for complete search history.

(56) References Cited

U.S. PATENT DOCUMENTS

| | | | |
|---|---|---|---|
| 4,292,108 A | 9/1981 | Weiss et al. | |
| 5,078,005 A | 1/1992 | Krempel et al. | |

(Continued)

FOREIGN PATENT DOCUMENTS

| | | | | |
|---|---|---|---|---|
| AU | WO2007/115363 | * | 10/2007 | ............. G01M 3/02 |
| AU | WO2009/065175 | * | 5/2009 | ............. G01M 3/26 |

(Continued)

OTHER PUBLICATIONS

International Preliminary Report on Patentability mailed Oct. 4, 2012 in PCT/EP2011/001429 and English translation.

(Continued)

*Primary Examiner* — Philip Tucker
*Assistant Examiner* — John Blades
(74) *Attorney, Agent, or Firm* — Greer, Burns & Crain, Ltd.

(57) ABSTRACT

An arrangement for monitoring the functionality of a structural adhesive layer to be fabricated between a first surface of a stiffening element and another component. A sensor block is bonded to a second surface of the stiffening component opposite to the first surface. The area of the structural adhesive layer incorporates a plurality of air openings and vacuum openings that vertically extend through the stiffening component and structural adhesive layer and the sensor block. The air openings are interconnected among each other by at least one air channel, and the vacuum openings by at least one vacuum channel. At least one of the channels is connected to an evaluator unit to detect a failure of the structural adhesive layer.

7 Claims, 5 Drawing Sheets

(51) Int. Cl.
*G01M 3/26* (2006.01)
*G01M 5/00* (2006.01)
*B26F 1/24* (2006.01)
*B32B 38/04* (2006.01)

(56) References Cited

U.S. PATENT DOCUMENTS

| | | | |
|---|---|---|---|
| 5,246,520 A | 9/1993 | Scanlon et al. | |
| 5,770,794 A | 6/1998 | Davey | |
| 8,196,453 B2* | 6/2012 | Walker et al. | 73/37 |
| 8,353,197 B2* | 1/2013 | Laxton et al. | 73/37 |
| 8,413,485 B2* | 4/2013 | Bach | B32B 3/00 |
| | | | 73/37 |
| 2002/0002866 A1 | 1/2002 | Davey | |
| 2002/0029614 A1* | 3/2002 | Davey | G01M 3/3254 |
| | | | 73/37 |
| 2009/0113994 A1* | 5/2009 | Walker | G01M 3/26 |
| | | | 73/40 |

FOREIGN PATENT DOCUMENTS

| | | |
|---|---|---|
| CN | 201 360 470 | 12/2009 |
| FR | 2 655 732 | 6/1991 |
| WO | WO 01/84102 | 11/2001 |

OTHER PUBLICATIONS

International Search Report for PCT/EP2011/001429 mailed Nov. 29, 2011.

* cited by examiner

STIFFENING COMPONENT AND METHOD AS WELL AS COMBING TOOL

CROSS-REFERENCES TO RELATED APPLICATIONS

This application claims the benefit of the U.S. Provisional Application No. 61/316,389, filed on Mar. 23, 2010, and of the German patent application No. 10 2010 012 342.0 filed on Mar. 23, 2010, the entire disclosures of which are incorporated herein by way of reference.

BACKGROUND OF THE INVENTION

The invention relates to a stiffening component for monitoring the functionality of a structural adhesive layer to be fabricated between the latter and another component.

In addition, the invention relates to a method for manufacturing a structural adhesive layer between such a stiffening component and another component, which can be checked in particular with respect to its functionality. Finally, the invention relates to a combing tool, in particular for implementing the method.

Increasing use is being made of CFRP components in modern aircraft construction. The CFRP components fabricated by suppliers are adhesively bonded in the aircraft structures to be manufactured within a time-critical production phase. Sensors for nondestructively monitoring the functionality of the adhesive bonds established in this way (so-called "NDT", nondestructive testing) during the production process and during ongoing airline operations are currently not integrated into the assemblies, among other reasons for cost considerations. Such sensors, for example which can be so-called "SHM sensors" (structural health monitoring sensors), are advantageous, however, since the currently available numerical calculation algorithms for determining the load-bearing capacity of CFRP components and their adhesive bonds do not have the level of accuracy necessary to completely exhaust the weight saving potential of the CFRP assemblies in comparison to the classic aluminum structure. In the case of CFRP components, this means that an additional level of mechanical safety must be provided by increasing the material thickness of the component and/or reinforcing the adhesive bonds in order to offset the inevitable calculation uncertainties. This generally results in an undesirable increase in weight of the CFRP component.

In addition, the process of manufacturing large-scale, complex CFRP components is extremely time-critical, since the curing processes for the utilized duroplastics, such as the widely used epoxy resins, have narrow tolerances in terms of time. As a consequence, prior art does not yet make it possible to integrate a complex array of sensors for structural health monitoring into the CFRP assemblies during the manufacturing process.

WO 01/84102 A1 discloses a vacuum system and a method for the detection of cracks and acquisition of crack propagation in components and structures. However, the previously known system is not provided for continuously monitoring a structural adhesive layer between two adhesively joined components. In addition, the vacuum system cannot be integrated into a high number of structural components without any loss of time.

SUMMARY OF THE INVENTION

Therefore, an object of the invention is to create a stiffening component for generating complex, large-scale components, in particular CFRP assemblies, which is already equipped with sensors for monitoring the functionality of the adhesive bonds to be fabricated during the process of its manufacture. In addition, an object of the invention is to indicate a method for manufacturing such a complex CFRP component, as well as a combing tool.

An object according to the invention is initially achieved by means of a stiffening component according to claim 1.

Because the area of the structural adhesive layer incorporates a plurality of air openings and vacuum openings that intersperse the stiffening component and structural adhesive layer, as well as a sensor block, and the air openings are interconnected by at least one air channel, and the vacuum openings by at least one vacuum channel, wherein the channels run in the sensor block, and at least one of the channels can be connected to an evaluator unit to detect a failure of the structural adhesive layer, the stiffening component as supplied by the manufacturer already has the desired monitoring system (SHF sensor array), which makes it possible to check the function of the structural adhesive layer already during the manufacturing process, and beyond that during the operation of the aircraft, if need be. In an advantageous manner, the stiffening component according to the invention can be used in modern vertical stabilizers, wings or horizontal stabilizers, which can only be checked for detached adhesive layers with great difficulty, if at all. Furthermore, the stiffening component can be used in all technical fields, for example in shipbuilding and vehicle construction, as well as in the area of regenerative energy generation, which require a continuous or case-by-case monitoring of structural adhesive bonds.

In the measuring principle employed here, an error leads to a difference in pressure between an air channel with a plurality of air boreholes that are exposed to a normal ambient air pressure, i.e., in contact with the atmosphere, and a vacuum channel with a plurality of vacuum boreholes, which exhibit a reduced air pressure by comparison to the air boreholes. The channels pneumatically operatively interact with the structural adhesive layer between the stiffening component and another component by way of the air and vacuum boreholes. Any change, no matter how slight, in the measured difference in pressure between the air channel and vacuum channel in the event of an error is evaluated and displayed by means of an evaluator unit, for example which is connected to the vacuum channel via a hose line with an adapter. To this end, the evaluator unit continuously measures the difference in pressure between the ambient air pressure and the current pressure in the vacuum channel. A vacuum pump integrated into the evaluator unit is typically dimensioned in such a way that a constant pressure difference on the order of 200 hPa (200 mbar) usually sets in between the vacuum channel and air channel. Other constant pressure difference values ranging from 200 hPa to 800 hPa are also possible. For example, one typical error that could be detected by the pneumatic SHM sensor array integrated into the stiffening component would involve an at least regional detachment of the structural adhesive layer from one of the joined components. All air boreholes, vacuum boreholes, air and vacuum channels are constituents of the sensor block or stiffening component, making them very robust vis-a-vis damaging environmental influences, and therefore resistant to failure.

As a result of this special configuration of the stiffening component, the latter can be incorporated directly into a production line for CFRP components without any appreciable time delay, for example meaning adhesively bonded with other CFRP components. After the stiffening component has been adhesively bonded with the other component, all that need be done in a final procedural step is to put on a cover plate to establish an airtight seal for the air channels and vacuum channels. The vacuum sensor array integrated into the stiffening component makes it possible to monitor the structural adhesive layer during airline operations, if necessary continuously, even for new types of CFRP structural components, which contain hard resistance foam components, and cannot be checked for detached adhesive layers and/or delamination, for example through conventional ultrasound inspection. Furthermore, the invention eliminates the need for a plurality of manual, and hence cost-intensive, inspection procedures during maintenance operations. In addition, the stiffening component permits the monitoring of structural adhesive bonds, which, while they could be analyzed with existing conventional inspection technology, are difficult, if not impossible to access for reasons of space. The evaluator unit can be connected with the sensor block either permanently or on a case-by-case basis, i.e., when the structural adhesive bond must be inspected.

In a prefabricated (delivery) state of the stiffening component "with built-in intelligence", the at least one sensor block is adhesively bonded in the region of the structural adhesive layer to be manufactured, wherein the air and vacuum openings completely (vertically) intersperse the stiffening component and sensor block, and empty into the air and vacuum channels, which have also already been incorporated. In addition, the combing tool has been inserted into the air and vacuum openings, and fixed on the sensor block.

An advantageous further development of the stiffening component provides that the evaluator unit exhibits at least one vacuum pump, so as to lower an air pressure in the vacuum channel to a value below the ambient air pressure.

In the case of a malfunction, this allows air from the environment to pass through the bad spot until into the vacuum openings, and from there into the vacuum channel. A resultant pressure change in the vacuum channel is relayed to the evaluator unit by means of a hose hooked up to perform the inspection, there electronically acquired, for example by a pressure sensor, and displayed for a user. As an alternative, the evaluator unit can contain a compressor to generate a highly constant excess pressure in the air channel in relation to the ambient air pressure, wherein the evaluator unit is connected with the air channel via a hose line, and ambient air pressure prevails in the vacuum channel. If even just a slight drop in pressure arises in the air channel, it points to a defect in the area of the structural adhesive layer.

A further development of the stiffening component provides that the sensor block is attached to an upper side of the stiffening component, in particular adhesively bonded with an adhesive layer, and that a combing tool can be inserted into the sensor block.

As a result, the monitoring sensor array for monitoring the structural adhesive layer is already provided by the manufacturer as an integral constituent of the stiffening component, and can be incorporated directly into time-critical production lines for CFRP components. An external supplier preferably already integrates the monitoring sensor array into the stiffening component, which can be a stringer or a rib, for example. The inserted combing tool safeguards the fine vacuum and air openings against contamination during transport and storage. In addition, adhesive is prevented from penetrating into the boreholes while adhesively bonding the stiffening component with an additional structural component. For this purpose, the combing tool, depending on the arrangement of the air and vacuum openings, exhibits two rows of borehole pins (dowel pins) arranged parallel to each other and spaced apart from each other, for example, whose selected diameter is slightly less than or equal to the diameter of the air and vacuum boreholes. As an alternative, a light press fit can be provided, so as to ensure a sufficiently strong and tight fit of the combing tool on the stiffening component or sensor block during its further processing.

In another embodiment, the air openings and vacuum openings are designed as air and vacuum boreholes, which each exhibit a diameter of up to 1 mm, and are each preferably positioned along at least one row of boreholes spaced apart from each other by a respective borehole distance of between 1 mm and 1,000 mm (1 m).

The air and vacuum openings are preferably designed as boreholes, in particular to simplify the production process. The openings can exhibit a shape deviating from this, for example be configured as oblong holes, slits or grooves.

The specified dimensions of the air and vacuum boreholes ensure a sufficiently dense monitoring grid for seamlessly monitoring the structural adhesive layer, along with a sensitive enough response characteristic in the event of an error. Furthermore, the dimensioning prevents false alarms caused by the suppression of excessively small pressure fluctuations in the vacuum channel.

Another advantageous further development of the stiffening component provides that the at least one air channel and at least one vacuum channel run side by side.

This makes it easy to manufacture the channels from the standpoint of production, for example by milling grooves having a rectangular cross sectional geometry into the sensor block. However, the grooves can exhibit any conceivable cross sectional geometry deviating from the rectangular shape. The channels preferably run parallel to each other, and are spaced apart from each other. Basically, the channels can also have a progression that deviates from a straight line, for example, exhibit a meandering configuration.

In another embodiment of the stiffening component, the sensor block is sealed pressure tight with at least one cover plate, in particular one adhesively bonded by means of an adhesive layer.

This provides the air channels and vacuum channels with an air- and pressure-tight seal, so that no false air can get to the evaluator unit, which would result in false alarms. In a second procedural alternative in which the sensor block is adhesively bonded to the stiffening component so that it turns, i.e., rotates by 180° around its longitudinal axis, the cover plate can be discarded, since the open channels point downward.

In another embodiment of the stiffening component, a calibration channel is at least sectionally arranged between the at least one air channel and at least one vacuum channel.

The calibration channel is used to compensate for influences exerted by pressure and temperature fluctuations on the monitoring result. To this end, the calibration channel is connected with the evaluator unit by means of a hose line. By calculating the difference between the current pressure value in the calibration channel and the accompanying pressure value in the vacuum channel, the influences of pressure and temperature fluctuations are subtracted out.

In addition, the object according to the invention is achieved with a method of the kind described in claim 8 involving the following steps:

a) Adhesively bonding a sensor block containing at least one air channel and at least one vacuum channel to the stiffening component, b) Incorporating a plurality of continuous air openings and vacuum openings into the sensor block and stiffening component, c) Inserting at least one combing tool with a plurality of borehole pins into the air openings as well as the vacuum openings, and temporarily securing the combing tool to the sensor block, d) Adhesively bonding the additional component with the stiffening component, wherein the borehole pins of the combing tool are pressed through the structural adhesive layer up to an upper side of the component, e) Removing the combing tool from the stiffening component, and f) Adhesively bonding a cover plate onto the sensor block.

This sequence of procedural steps makes it possible to integrate the SHM sensor array into the stiffening component in advance prior to its installation, as well as to establish a structural adhesive bond between the stiffening component thusly equipped in advance and another component, thereby enabling a permanent functional control of the structural adhesive layer in the assembled component. Without causing any delays in the production process, the new type of stiffening component can here be incorporated in high numbers into an existing, usually time-critical industrial production line for large-scale CFRP components, while retaining the existing means of production.

In procedural step a), the sensor block encompassing at least one air channel and at least one vacuum channel is first adhesively bonded to the stiffening component in the area of the structural adhesive layer to be fabricated. In procedural step b), a plurality of continuous air and vacuum openings is introduced into the air and vacuum channels of the sensor block and the stiffening component, wherein the air and vacuum openings completely intersperse the stiffening component in equal measure. In cases where the vacuum and air openings are designed as boreholes, the sensor block can also be provided in advance with continuous boreholes, in such a way that the sensor block itself with the predrilled air boreholes and vacuum boreholes serves as the drilling template for the stiffening component to be provided with the air boreholes and vacuum boreholes. In procedural step c), the at least one combing tool exhibiting a plurality of borehole pins is inserted into the air and vacuum openings. This reliably prevents adhesives from penetrating into the openings in the joining process. For example, the combing tool is temporarily fixed on the sensor block by means of a latching bracket that can be readily detached, if need be. If the vacuum openings are designed as boreholes, the borehole pins of the combing tool have a slightly excess length relative to the air and vacuum boreholes for latching purposes. If the air and vacuum openings exhibit a geometry deviating from the cylindrical shape, for example as is the case for oblong holes, slits or grooves, the borehole pins each have a configuration that corresponds thereto, i.e., at least regionally exhibits a positive fit. In order to seal the openings, there is at least a regional positive fit between the latter and the borehole pins of the combing tool (slight press fit). In procedural step d), the stiffening component usually fitted in this way in advance by a supplier is adhesively bonded with the additional component while generating the structural adhesive layer. The borehole pins of the combing tool are here pressed through the structural adhesive layer until reaching the upper side of the additional component. To this end, the borehole pins each exhibit small tips in the region of their lower ends, and are also spring-mounted in the combing tool. The combing tool is removed from the stiffening component by detaching the latching bracket in procedural step e), while a cover plate is adhesively bonded to the sensor block in procedural step f), so as to form vacuum channels and air channels with an airtight seal.

A further development of the invention provides that at least one of the channels of the sensor block is at least temporarily connected to an evaluator unit to check the structural adhesive layer.

In this way, the structural adhesive layer between the stiffening component and the additional component can be checked for integrity if so required, for example during inspection and maintenance operations to be routinely performed. This brings with it weight-related advantages, since the evaluator unit does not always have to be carried along. If necessary, the evaluator unit can also remain permanently connected with the stiffening component or the sensor block integrated therein, so as to continuously monitor the structural adhesive layer during ongoing operations (under a load). The connection is established by means of a hose line that joins the vacuum channel and evaluator unit.

The object is further achieved by means of a combing tool.

The combing tool exhibits a plurality of projections that can be incorporated into the air and vacuum openings, making it possible to prevent the air and vacuum openings from becoming clogged during the adhesive bonding process, and thus to avert a subsequent malfunction by the sensor block in the stiffening component. To this end, the geometric configuration of the combing tool projections corresponds with the shape of the air and vacuum openings, for example which can be designed as cylindrical boreholes, oblong holes, slits or longitudinal grooves, i.e., there is a slight press fit. In addition, the combing tool prevents foreign particles from penetrating into the air and vacuum openings during the storage and transport of the stiffening component.

A further development of the combing tool provides that the projections are designed as cylindrical borehole pins, and that each borehole pin is spring mounted so that it can vertically shift in a bearing borehole by means of a compression spring.

The cylindrical configuration of the borehole pins initially makes it easier to manufacture the combing tool from a production standpoint. In addition, the spring-mounted borehole pins accommodated in the combing tool are pressed through the then still soft structural adhesive layer during the adhesive bonding process with a force defined by the springs, and here at the same time slightly scratch the upper side of the additional component, thereby making it possible to completely monitor the structural adhesive layer over its entire height. In order to achieve this, the lower ends of the borehole pins preferably exhibit small tips. After the structural adhesive layer has hardened, the combing tool secured to the sensor block by means of a clamp mounting can again be removed from the latter by applying a limited tensile force.

DETAILED DESCRIPTION OF THE PREFERRED EMBODIMENTS

Figure 1:
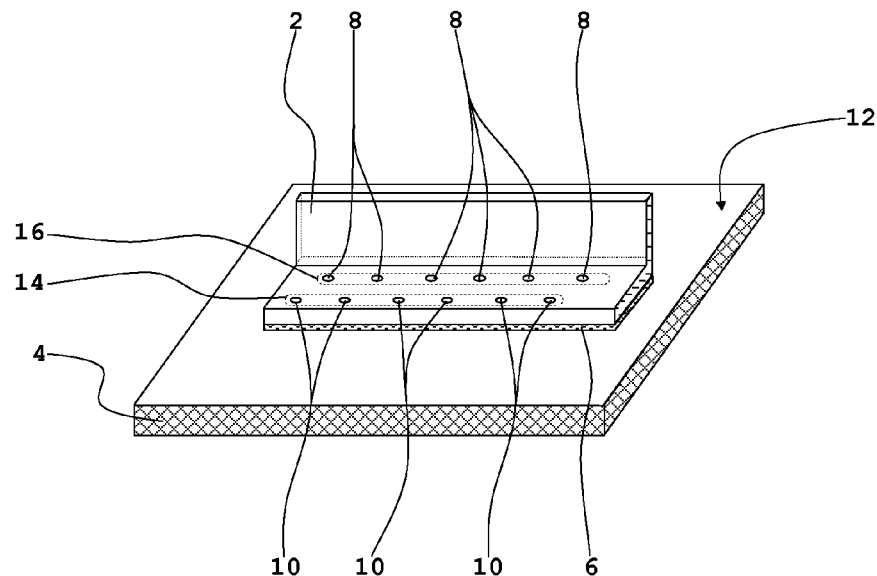
FIG. 1 a perspective view of an exemplary stiffening component adhesively bonded to a component, FIG. 2 a simplified schematic diagram presenting the inner structure of the stiffening component, FIG. 3 a sectional view of the stiffening component adhesively bonded to an additional (structural) component, FIG. 4 a schematic diagram presenting how the bad spot monitor works ("vacuum-SHM monitoring"), FIG. 5 a sectional view through a combing tool according to the invention, and FIG. 6-9 a schematic diagram presenting the course of the procedure.

FIG. 1 illustrates a schematic view of the stiffening component according to the invention with air and vacuum boreholes arranged in two rows, which is adhesively bonded on another component.

A stiffening component 2, specifically a stringer having an L-shaped cross sectional geometry in the exemplary embodiment shown, is adhesively bonded on a component 4, for example the fuselage skin or vertical stabilizer skin of an aircraft, by means of a structural adhesive layer 6. The stiffening component 2 can exhibit a cross sectional shape deviating from the depicted L-shaped cross sectional geometry, for example a T-shaped, a U-shaped, a C-shaped or a Z-shaped cross sectional geometry. For example, the stiffening component and/or the additional component 4 can be fabricated with a carbon fiber reinforced plastic (CFRP), a fiber composite or a metal material. According to the invention, the stiffening component 2 incorporates a plurality of continuous air and vacuum openings, which are here designed as cylindrical air boreholes 8 and vacuum boreholes 10, which intersperse through the structural adhesive layer 6 until they reach an upper side 12 of the component 4. The air and vacuum boreholes 8, 10 are each arranged in borehole rows 14, 16 in the area of the structural adhesive layer 6. The borehole rows 14, 16 are uniformly parallel to each other and spaced apart from each other, and the air boreholes 8 and vacuum boreholes 10 are each positioned along the borehole rows 14, 16 so as to be spaced uniformly apart from each other. A deviating arrangement of boreholes is possible.

Figure 2:
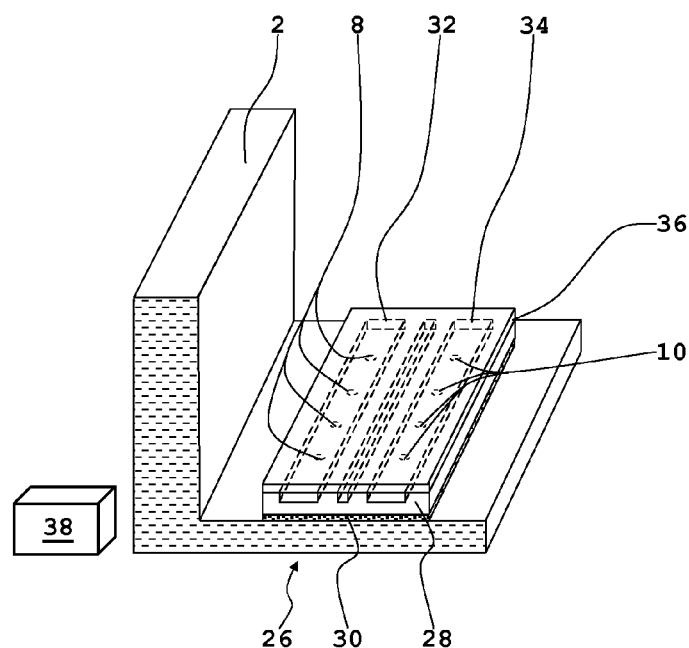

FIG. 2 shows a perspective detailed view of the stiffening component according to the invention.

In region 26 of the structural adhesive layer to be fabricated, a sensor block 28 is adhesively bonded to the stiffening component 2 by means of an adhesive layer 30. The sensor block 28 can be made out of a plastic material and/or metal. An air channel 32 and vacuum channel 34 run parallel to each other and spaced apart from each other within the sensor block 28. The air boreholes 8 or vacuum boreholes 10 are each interconnected by way of the air channel 32 or vacuum channel 34. The sensor block 28 is upwardly sealed airtight with a cover plate 36 preferably adhesively bonded thereto, thereby giving rise to an air channel 32 and vacuum channel 34, which each have an approximately rectangular cross section. An evaluator unit 38 is connected with the vacuum channel 34 by a hose line (not shown).

The evaluator unit 38 incorporates a vacuum pump (also not shown) that maintains a constant air pressure value in the vacuum channel 34, for example one that is 200 hPa (200 mbar) less than the ambient air pressure prevailing in the air channel 32, e.g., of 1,013 hPa. Any change in this normally constant difference in pressure indicates that the integrity of the structural adhesive layer is at least regionally impaired, for example that the structural adhesive layer 6 has become detached. In order to evaluate this difference in pressure between the air channel 32 and vacuum channel 34, the evaluator unit 38 contains pressure sensors, measuring transducers, an electronic computer unit and signaling units, for example displays and/or audio signal generators (not depicted in any greater detail).

Figure 3:
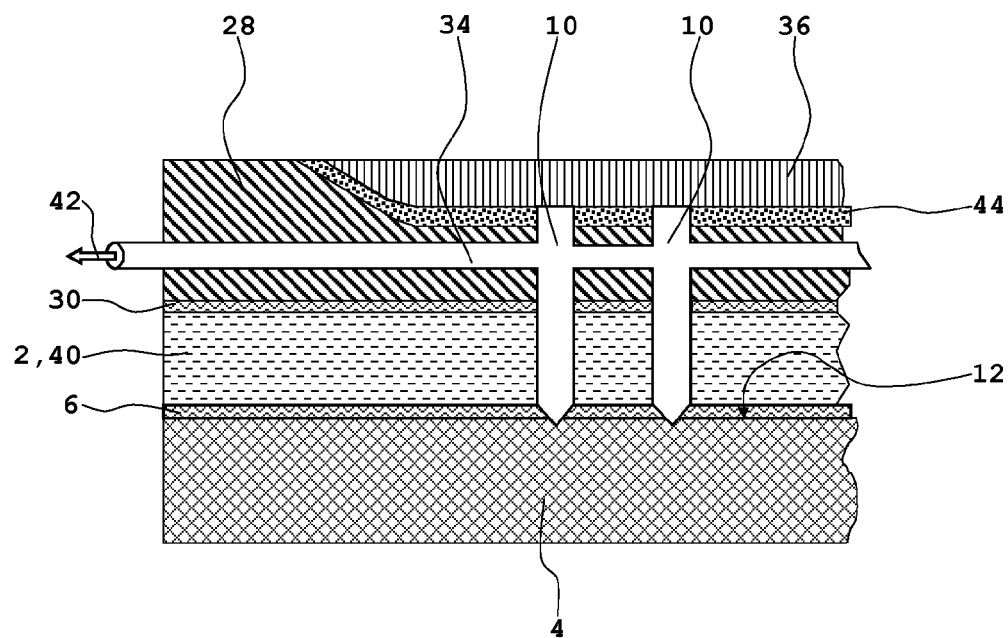

FIG. 3 presents a sectional view of the stiffening component adhesively bonded to a (structural) component.

The stiffening component 2 is adhesively bonded to the additional component 4 by means of the structural adhesive layer 6. The sensor block 28 is adhesively bonded to the stiffening component 2 by means of the adhesive layer 30. The vacuum channel 34 with vacuum boreholes 10 runs in the sensor block 28. As evident, the vacuum boreholes 10 completely intersperse a foot 40 of the stiffening component 2 as well as the structural adhesive layer 6, and in addition penetrate or "scratch" into the latter a little bit, specifically as far as under the upper side 12 of the component 4. This yields an especially reliable and complete detection of any detachment by the structural adhesive layer 6.

The undesignated penetration depth by the vacuum boreholes 10 into the component 4 lies between 0.1 mm and 0.5 mm. As denoted by the white arrow 42, the vacuum channel 34 is connected with the vacuum pump integrated into the evaluator unit 38 by means of a hose line (not shown). When the air pressure in the vacuum channel 34 is lower than the ambient air pressure by a constant level of 200 hPa, for example, the functionality of the structural adhesive layer 6 is unrestricted, i.e., there are no detachments of the structural adhesive layer 6 between the stiffening component 2 and component 4, not even regionally. Another adhesive layer 44 is used to adhesively bond a cover plate to the sensor block 28, so as to seal the channels airtight. The adhesive layer 44 can be covered with a removable protective film (not shown), which prevents the adhesive layer 44 from becoming contaminated by foreign particles while storing, transporting and joining the stiffening component 2.

Figure 4:
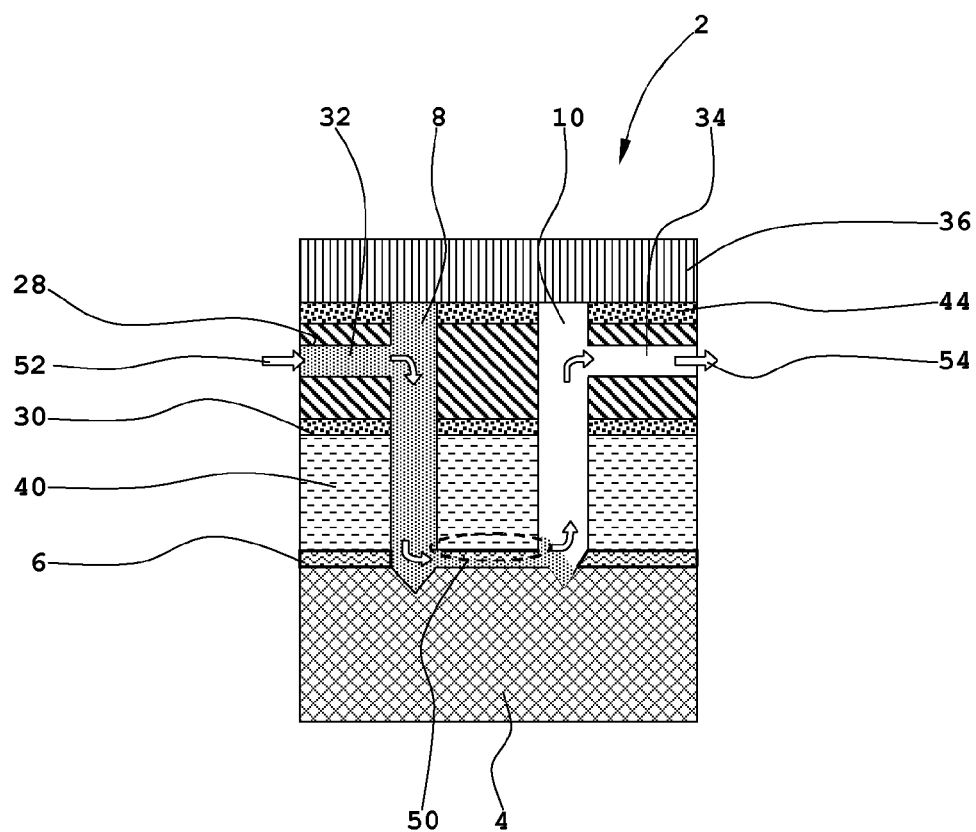

FIG. 4 illustrates the basic principle underlying how the stiffening component according to the invention operates upon detecting that the structural adhesive layer has detached from the component.

The stiffening component 2 is adhesively bonded to the component 4 by means of the structural adhesive layer 6. The sensor block 28 joined together with the foot 40 of the stiffening component 2 by means of the adhesive layer 30 incorporates the air and vacuum channels 32, 34, as well as the air and vacuum boreholes 8, 10. The two channels 32, 34 are covered at the top by the cover plate 36 adhesively bonded by means of the adhesive layer 44. The structural adhesive layer 6 has a detached section 50, i.e., a bad spot that impairs the mechanical strength between the stiffening component 2 and component 4. In the error depicted, the (ambient) air streams from the air channel 32 until into the structural adhesive layer 6 via the air borehole 8, as denoted by the arrow 52. From there, the air seeps through the structural adhesive layer 6 and detached section 50 and into the vacuum borehole 10. The air continues to flow from the vacuum borehole 10 into the vacuum channel 34, and from there, as denoted by arrow 54, to the evaluator unit 38 connected thereto (not shown). As a result, the air pressure in the area of the vacuum channel 34 rises, and this change in air pressure is detected and visually and/or acoustically signaled by means of the evaluator unit 38.

Figure 5:
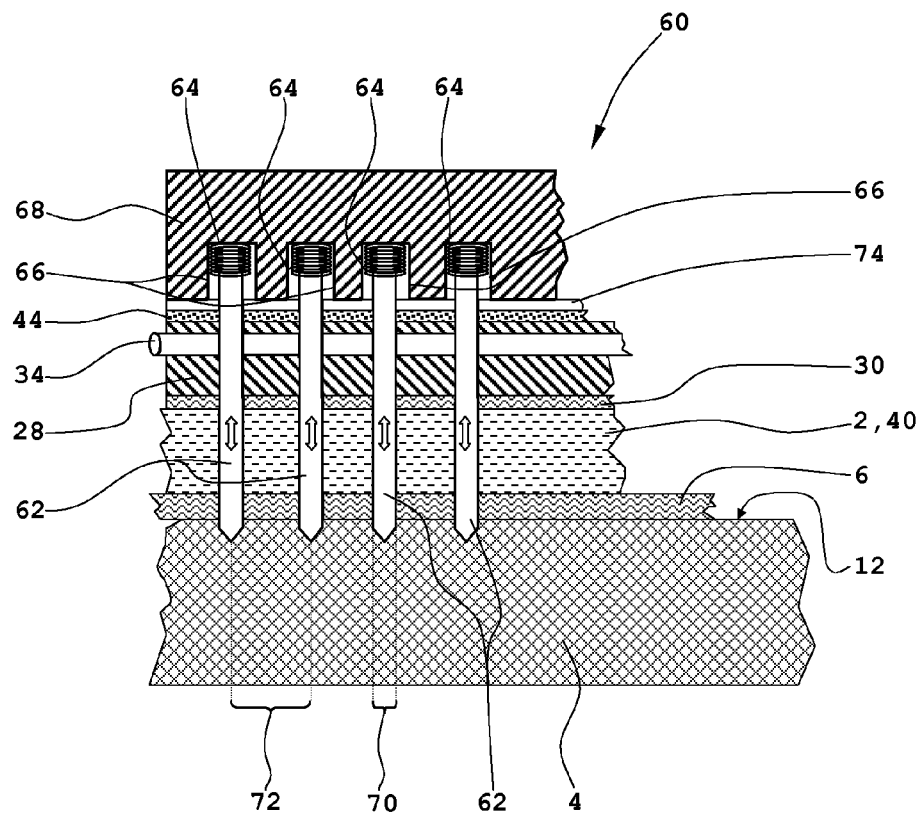

FIG. 5 presents a sectional view through a combing tool, which seals the air and vacuum boreholes in the process of adhesively bonding the stiffening component, so as to prevent the boreholes from becoming contaminated by the adhesive, and the sensor block from malfunctioning as a result. In addition, the combing tool protects the sensitive boreholes against penetration by dirt particles while transporting and storing the stiffening component.

The combing tool 60 has a plurality of borehole pins 62, which are spring-mounted in bearing boreholes 66 of a housing 68 by means of compression springs 64 so that they can shift vertically, as denoted on FIG. 5 with the small white double arrows. The lower ends of the essentially cylindrical borehole pins 62 each have tips to make it easier to penetrate through the structural adhesive layer 6 and scratch the surface 12 of the component 4. A diameter 70 of the borehole pins 62 measures a respective 1 mm, and a distance 72 between the rowed borehole pins measures a respective 3 mm. A slightly larger diameter was correspondingly selected for the boreholes not provided with reference numbers on FIG. 5 to provide a better graphic overview, so as to ensure an easy introduction of borehole pins into the air boreholes and vacuum boreholes. As an alternative, there can be a slight press fit between the air and vacuum boreholes and the diameter of the borehole pins 62.

As already explained in the description to FIG. 1, a distance between the air and vacuum boreholes corresponds to the respective 3 mm distances 72 between the borehole pins 62 in the combing tool 60. At the same time, the compression springs 64 limit the press-in force exerted by the borehole pins 62 on the surface 12 of the component 4. The diameters 70 of the borehole pins 62 or the undesignated diameters of the air and vacuum boreholes 8, 10 can basically range between 0.25 mm and 3 mm, and their distances can lie within an interval of between 1 mm and 1,000 mm. The combing tool 60 rests on a removable protective film 74, which protects the adhesive layer 44 to be used later for adhesively bonding the cover plate 36 against contaminants. The sensor block 28 is non-detachably secured to the foot 40 of the stiffening component 2 by means of the adhesive layer 30. The foot 40 of the stiffening component 2 is connected with the component 4 by means of the structural adhesive layer 6. The vacuum channel 34 runs inside the sensor block 28.

Reference will at the same time be made to FIGS. 6 to 9 in the further course of the description, based upon which the sequence of a first procedural variant for manufacturing an adhesive bond accompanied by the creation of a structural adhesive layer between the stiffening component 2 and component 4 will be explained in greater detail.

Figure 6:
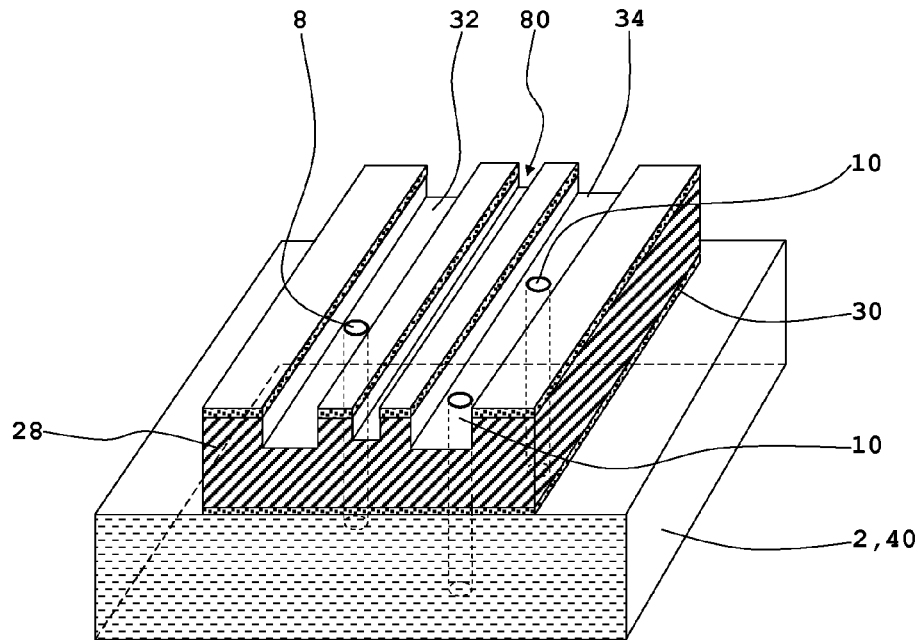

As may be gleaned from FIG. 6, the sensor block 28 is adhesively bonded to the foot 40 of the stiffening component (not shown in any more detail here) by means of the adhesive layer 30 in procedural step a). Preferably present in this procedural stage are the air channel 32 and vacuum channel 34, including a calibration channel 80 running centrally between the two. The calibration channel 80 is likewise connected with the evaluator unit 38 by way of a hose line (not shown), and used to balance out temperature and/or air pressure fluctuations in the ambient air, which would otherwise influence the detection result, and can result in false alarms and/or undetected detachments of the structural adhesive layer.

The continuous air boreholes 8 as well as the continuous vacuum boreholes 10 are subsequently introduced into the sensor block in procedural step b). All cases involve through boreholes, i.e., so-called "TTT" boreholes (through-the-thickness boreholes). As an alternative, the boreholes can already have been introduced into the sensor block 28 before being adhesively bonded thereto, so that these preliminary boreholes can at the same time be used as a guide or borehole template after the sensor block 28 has been adhesively bonded to the foot 40 of the stiffening component 2. Accordingly, the vacuum channel 32 and air channel 34 can optionally be introduced into the sensor block 28, for example via recessing, before or after it has been adhesively bonded.

Figure 7:
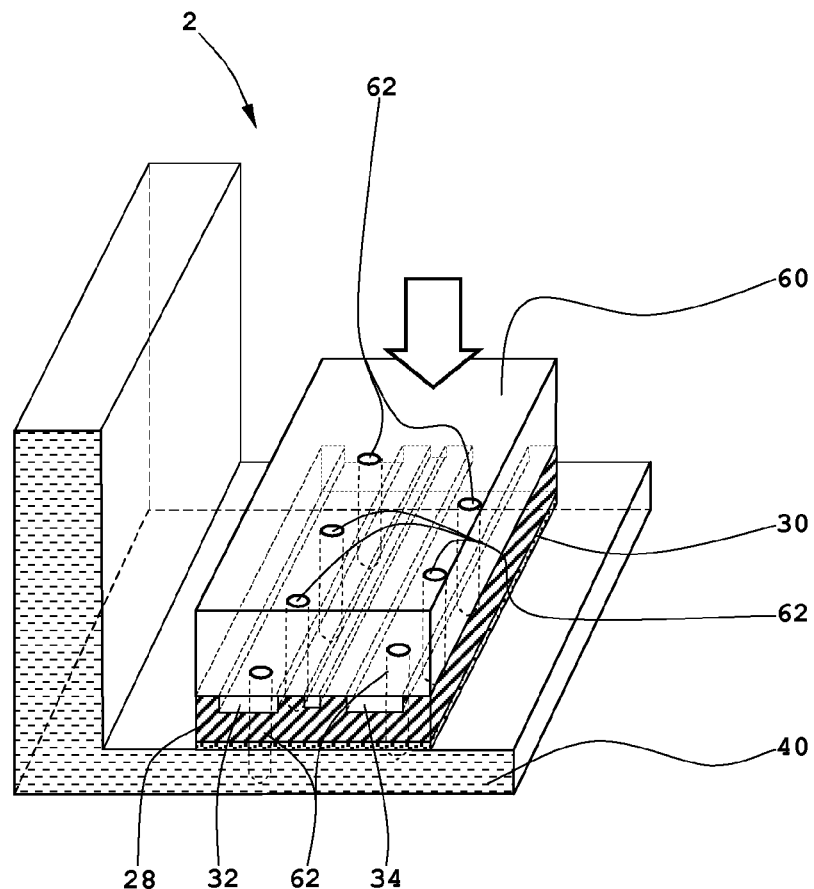

According to FIG. 7, procedural step c) involves inserting the combing tool 60 into the air boreholes and vacuum boreholes that were prefabricated in this manner, but not designated here, as denoted by the large white arrow. Prior to insertion, all borehole pins 62 are provided with a separating agent, so that the combing tool 60 can be removed after the structural adhesive layer has been completely manufactured. The state of the stiffening component 2 depicted on FIG. 7, in which the sensor block with the air channel 32 and vacuum channel 34 has already been adhesively bonded to the foot 40 of the stiffening component 2 by means of the adhesive layer 30, and the combing tool 60 with its plurality of borehole pins 62 has been inserted into the vacuum and air boreholes, and also temporarily secured to the sensor block 28 by way of a latching bracket (not shown), preferably corresponds to the delivery state, in which the final adhesive bonding of the stiffening component 2 to the additional component 4 (not shown here) to form a single component takes place.

Figure 8:
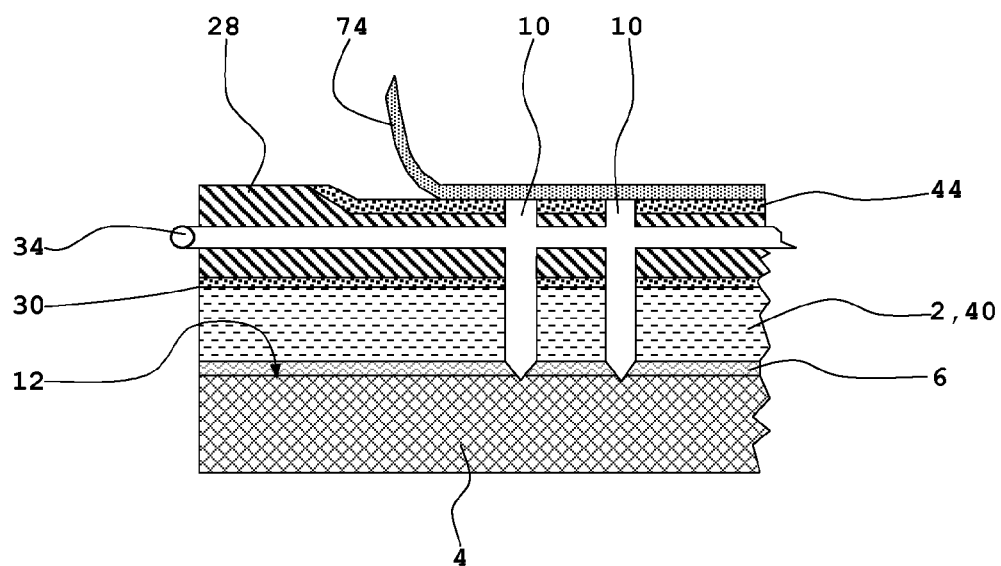
Figure 9:
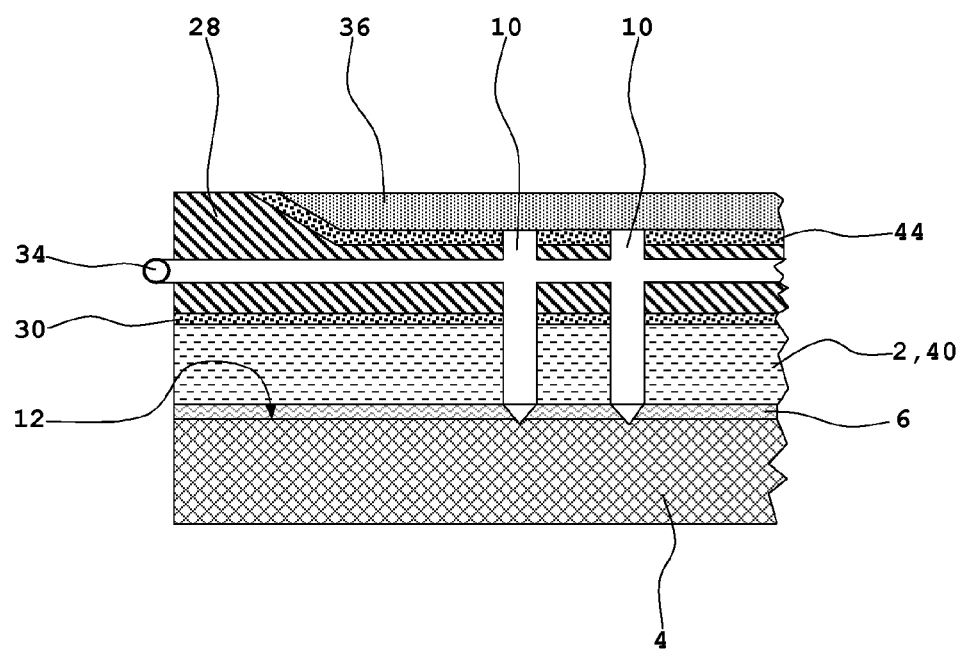

As depicted on FIGS. 8 and 9, the foot 40 of the stiffening component 2 was adhesively bonded to the component 4 in procedural step d) by means of the respective structural adhesive layer 6. It is crucially important when carrying out the adhesive bonding process that the borehole pins 62 of the combing tool 60 be pressed both through the still malleable structural adhesive layer 6 and a short way into the upper side 12 of the component 4, in order to achieve a complete monitoring (so-called "health monitoring") of the structural adhesive layer 6 with an eye toward its potential failure. As already described above, the sensor block 28 with the air and vacuum boreholes contained therein, of which only the vacuum boreholes 10 are shown here, are adhesively bonded to the foot 40 or base flange of the stiffening component 2 by means of the adhesive layer 30. An adapter (not shown) is used to join a hose line (also not shown) to the vacuum channel 34 for purposes of connection with the evaluator unit 38.

In the procedural step e) illustrated on FIG. 8, the combing tool 60 has already been removed from the stiffening component 2 or sensor block 28. The protective film 74 was already partially removed from the underlying adhesive layer 44 in preparation for the concluding procedural step f), in which the cover plate 36 is adhesively bonded to the sensor block 28 for hermetically sealing the vacuum channels and air channels, as well as the air and vacuum boreholes.

As opposed to FIG. 8, the process of adhesively bonding the component 4 and stiffening component 2 has completely ended in the procedural state depicted on FIG. 9, wherein the cover plate 36 has been adhesively bonded securely to the sensor block 28 by means of the adhesive layer 44, concluding the process.

In a second procedural variant not shown on the figures, the air and vacuum openings are first introduced into the stiffening component 2 in the region of the structural adhesive layer 6 to be fabricated in procedural step a). The combing tool 60 is inserted into the stiffening component 2 to seal the air and vacuum openings in procedural step b). The structural adhesive layer 6 between the component 4 and stiffening component 2 is created in procedural step c). The combing tool 60 is removed from the adhesively bonded components in procedural step d), and the final procedural step e) involves adhesively bonding the sensor block to the stiffening component 2 in the region of the structural adhesive layer 6 while in a position rotated by 180° in comparison to the first procedural variant, i.e., while reversed.

The step required in the first procedural variant for adhesively bonding the cover plate 36 to the sensor block 28 is omitted.

REFERENCE LIST

2 Stiffening component (stringer; rib)
4 Component (skin field)

6 Structural adhesive layer
8 Air borehole
10 Vacuum borehole
12 Upper side (component)
14 Borehole row
16 Borehole row
26 Region (later structural adhesive layer)
28 Sensor block
30 Adhesive layer (sensor block)
32 Air channel
34 Vacuum channel
36 Cover plate
38 Evaluator unit
40 Foot (stiffening component)
42 Arrow
44 Adhesive layer (cover plate)
50 Detachment (bad spot on structural adhesive layer)
52 Arrow
54 Arrow
60 Combing tool
62 Borehole pin
64 Compression spring
66 Bearing borehole
68 Housing (combing tool)
70 Diameter (borehole pin)
72 Distance (borehole pins)
74 Protective film
80 Calibration channel

The invention claimed is:

1. An arrangement for monitoring the functionality of a structural adhesive layer fabricated between a first surface of a stiffening component and another component, comprising:
the stiffening component;
the structural adhesive layer fabricated between a first surface of the stiffening component and another component;
a sensor block bonded to a second surface of the stiffening component opposite to the first surface; and
a plurality of air openings and vacuum openings vertically extending through the stiffening component the structural adhesive layer and the sensor block,
wherein the air openings are interconnected among each other by at least one air channel, and the vacuum openings are interconnected among each other by at least one vacuum channel, and wherein the air and vacuum channels extend in the sensor block, and wherein the channels pneumatically operatively interact with the structural adhesive layer between the stiffening components and another component by way of the air and vacuum air openings, the arrangement further comprising an evaluator unit connected to at least one of the channels to detect a failure of the structural adhesive layer,
wherein the arrangement further comprises a combing tool having a plurality of borehole pins which are spring-mounted in bearing boreholes of a housing,
wherein the combing tool is configured to be inserted into the stiffening component such that the borehole pins penetrate through the structural adhesive layer and scratch a surface of the additional component.

2. The arrangement according to claim 1, wherein the evaluator unit comprises a vacuum pump for lowering an air pressure in the vacuum channel to a value lying below the ambient air pressure.

3. The arrangement according to claim 1, wherein the sensor block is attached to an upper side of the stiffening component and is adhesively bonded with an adhesive layer, and wherein the arrangement further comprises a combing tool which can be inserted into the sensor block.

4. The arrangement according to claim 1, wherein the air openings and vacuum openings are designed as air and vacuum boreholes, which each exhibit a diameter of up to 1 mm, and are each positioned along at least one row of boreholes spaced apart from each other by a respective borehole distance of between 1 mm and 1,000 mm.

5. The arrangement according to claim 1, wherein the at least one air channel and at least one vacuum channel run side by side.

6. The arrangement according to claim 1, wherein the sensor block is sealed pressure tight with at least one cover plate that is adhesively bonded by means of an adhesive layer.

7. The arrangement according to claim 1, wherein a calibration channel is at least sectionally arranged between the at least one air channel and at least one vacuum channel.

* * * * *